(12) United States Patent
Röper et al.

(10) Patent No.: US 8,618,511 B2
(45) Date of Patent: Dec. 31, 2013

(54) MARKING METHOD FOR THE REJECT MARKING OF TEST ELEMENTS (75) Inventors: Josef K. Röper, Neuhofen (DE); Werner Finke, Einhausen (DE); Martin Frank, Dirmstein (DE); Günter Schmidt, Lampertheim (DE); Siegfried Dick, Mannheim (DE); Peter Stubenbord, Neuhofen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 346 days.

(21) Appl. No.: 12/212,874

(22) Filed: Sep. 18, 2008

(65) Prior Publication Data

US 2009/0090874 A1 Apr. 9, 2009

(30) Foreign Application Priority Data

Sep. 19, 2007 (EP) .................................... 07116749

(51) Int. Cl.
  *G01N 21/00* (2006.01)
(52) U.S. Cl.
  USPC ...................................................... 250/474.1
(58) Field of Classification Search
  USPC ...................................................... 250/474.1
  See application file for complete search history.

(56) References Cited

U.S. PATENT DOCUMENTS

| 4,578,716 | A | 3/1986 | van Rijckevorsel et al. |
| 4,865,198 | A | 9/1989 | Butler |
| 5,286,362 | A | 2/1994 | Hoenes et al. |
| 5,708,247 | A * | 1/1998 | McAleer et al. ......... 204/403.05 |
| 6,045,567 | A * | 4/2000 | Taylor et al. .................... 606/181 |
| 6,168,957 | B1 * | 1/2001 | Matzinger et al. ............. 436/518 |
| 6,733,655 | B1 * | 5/2004 | Davies et al. .................. 205/775 |
| 2002/0082797 | A1 * | 6/2002 | Deweese et al. .............. 702/122 |
| 2002/0168317 | A1 * | 11/2002 | Daighighian et al. ....... 424/1.11 |
| 2003/0207441 | A1 * | 11/2003 | Eyster et al. ................ 435/287.1 |
| 2004/0015102 | A1 * | 1/2004 | Cummings et al. ........... 600/584 |
| 2004/0048359 | A1 | 3/2004 | Schmeling |
| 2005/0201897 | A1 * | 9/2005 | Zimmer et al. ............ 422/82.05 |
| 2006/0006574 | A1 * | 1/2006 | Lang et al. ..................... 264/165 |

(Continued)

FOREIGN PATENT DOCUMENTS

| CA | 2050677 | 4/2003 |
| EP | 0 132 790 A2 | 2/1985 |

(Continued)

OTHER PUBLICATIONS

Omicron Laserage Laserprodukte GmbH, "Omicron presents a new high-power UV-A LED module", Press Release No. Jul. 2006, 4 pages (including translation).

(Continued)

*Primary Examiner* — David Porta
*Assistant Examiner* — Shun Lee
(74) *Attorney, Agent, or Firm* — Krieg DeVault LLP (57) ABSTRACT

The test elements are provided that are adapted to detect at least one analyte in a sample. At least some of the test elements are provided with a defect marking which contains information about defectiveness of the test elements. The test elements include at least one radiation-sensitive material. The test elements are exposed to at least one radiation, the radiation being adapted to induce marking in the form of at least one optically detectable change in the radiation-sensitive material.

26 Claims, 4 Drawing Sheets

(56) References Cited

U.S. PATENT DOCUMENTS

| | | |
|---|---|---|
| 2007/0273928 A1* | 11/2007 | Robinson et al. ............ 358/3.01 |
| 2008/0029606 A1* | 2/2008 | Lewis ........................... 235/491 |
| 2008/0037273 A1* | 2/2008 | Muehlemann et al. ....... 362/581 |
| 2009/0212109 A1 | 8/2009 | Harttig et al. |

FOREIGN PATENT DOCUMENTS

| | | |
|---|---|---|
| EP | 0 678 308 A1 | 10/1995 |
| EP | 1 826 705 A1 | 8/2007 |
| JP | 60039561 | 3/1985 |
| JP | 1226533 A | 9/1989 |
| JP | 2001055537 A | 2/2001 |
| JP | 2001183558 A | 7/2001 |
| JP | 2002066770 | 3/2002 |
| JP | 2005056608 | 3/2005 |
| JP | 2006000865 | 1/2006 |

OTHER PUBLICATIONS

Giessen Friedberg University of Applied Sciences, "Fiber optic UV systems", Laser 2005, Halle B2, Stand 459, 4 pages (including translation).

Giessen Friedberg Univ of Applied Sciences, "UV-A light source with a flexible light guidance system", Achema 2006, Halle 1.2, Stand C5-F8, 3 pages (including translation).

Japanese Patent Application No. 238995/2008, Office Action dated Nov. 29, 2011 (translation-in-part), File No. JP-16697, Dispatched No. 812188, 5 pages.

Japanese Patent Application No. 238995/2008, Pending Claims, 3 pages.

* cited by examiner

MARKING METHOD FOR THE REJECT MARKING OF TEST ELEMENTS

CROSS-REFERENCE TO RELATED APPLICATIONS

Applicants claim foreign priority benefits under Title 35 U.S.C. §119 of European Patent Application No. EP 07116749.8 filed on 19 Sep. 2007, which is incorporated herein by reference in its entirety.

FIELD OF THE INVENTION

The invention relates to a marking method for marking defective test elements and to a production method for producing test elements, which involves a marking method according to the invention. The invention furthermore relates to a marking device, in particular for carrying out a marking method according to the invention, and to a production device for producing test elements, which comprises a marking device according to the invention. The invention furthermore relates to an analytical test instrument which uses a test element produced by the production method according to the invention. Such marking and production methods, marking and production devices and analytical test instruments are used particularly in chemical analysis and in medical technology. By means of the test elements, for example analytes such as e.g. metabolites in samples, particularly in liquid samples such as e.g. in blood, urine, in interstitial fluid or other bodily fluids, can be detected qualitatively and/or quantitatively. An essential application example of the present invention lies in the field of blood sugar diagnosis

BACKGROUND

In many fields of technology, natural science and medicine, analytes in samples must reliably be detected qualitatively and/or quantitatively. This is done in many cases with test elements, which react sensitively to one or more analytes. In particular, it is possible to use test elements which comprise at least one test material that changes at least one measurable property when the analyte is present in the sample, or upon contact with the analyte. These properties may for example, as mentioned in more detail below, be electrical and/or optical properties.

An essential application field of the present invention, albeit one to which the invention is not restricted, is medical diagnosis. For example, the monitoring of blood glucose concentrations is an essential part of daily life for diabetics. In this case the blood glucose concentration must rapidly and simply be determined generally several times per day, so that corresponding medical measures can be implemented if appropriate. In order not to restrict the daily life of a diabetic more than necessary, corresponding mobile instruments are often used which should be simple to transport and handle, so that the blood glucose concentration can be measured rapidly and simply but nevertheless reliably, for example in the workplace or in leisure time. Static instruments may however also be used, for example instruments which are designed for hospitals, medical practices or care institutions.

Various analysis instruments are currently on the market, which sometimes function according to different measurement methods. Various diagnostic methods are employed for this, for example optical or electrochemical measurement methods. The aforementioned test elements, which are usually provided in the form of test strips, are often an essential element of these measurement methods. For example, they may be electrochemical and/or optical test strips. Examples of electrochemical test strips are described, for example, in U.S. Pat. No. 5,286,362. Optical test elements are described, for example in CA 2,050,677. Other types of test elements are also known and may be used in the scope of the present invention, for example implantable test elements (see for example EP 0 678 308 B1). Instead of individual test elements, for example test strips or test tubes, test elements are also known which are held in a magazine or in another type of storage device. For example, a plurality of test elements may be rigidly connected together, for example in the scope of a test disc on which there are a plurality of test fields. Other types of multiple test elements are known, for example in the scope of band cassettes in which a multiplicity of test elements or test fields are arranged on a common band so that they may for example be used in succession. Other embodiments of magazines are drum magazines, in which a plurality of test elements are accommodated in a magazine drum. Other embodiments are also known.

The reliability of the analyte detection plays a crucial role in particular for quantitative detection methods in medical diagnosis. Thus, a range of further decisions generally depend on the result of the detection, for example a decision about insulin medication or a decision about another kind of medical treatment. To this extent efficient quality management is required in the production of the test elements, which reliably prevents defective test elements from being put into circulation or, if they are in circulation, from being used there. This quality management may involve a multiplicity of test methods which can subject the test elements to particular function tests already during the production process, or after production. For example, tests may be carried out which (for example by means of image recognition, electronic measurements, optical measurements or combinations of measurements) check particular functionalities of the test elements and thereby identify defective test elements with a certain probability.

The production of such test elements is generally a mass process, in which a multiplicity of test elements are produced on a large technical scale with a high throughput. When a defective test element is identified, it is therefore generally not possible to reject this test element directly. Methods are therefore known from the prior art in which test elements identified as defective are marked as being defective during or after the production method. Examples of such marking methods are disclosed in US 2004/0048359 A1, where defective regions are marked with a pen or marker. Another method known from the prior art is described in EP 0132790 A2. Here, a multiplicity of test elements are produced on a common band and, after a defect is found, a suitable marking in the form of a color point or a magnetic marking is applied so that the defective test element can subsequently be rejected simply and reliably.

In practice, however, the marking and production methods known from the prior art have numerous disadvantages. For instance, the known marking methods generally employ additional working substances and auxiliary substances, for example inks for the color points, paints, magnetic materials or similar materials. These additional working and auxiliary substances may however interact with the functionality of the test elements, and may for example influence the functionality of a test material (for example a test chemical for the detection of blood glucose or another metabolite). Thus, in general, safety of the working and auxiliary substances used for the marking must extensively be checked and confirmed, for example in order to obtain corresponding statutory approvals.

Another disadvantage of known methods is that many of the known application methods for the working and auxiliary substances, which are used for the marking, are complex and susceptible to error. For example, paints or inks for the marking may be applied by means of a printing method which, however, is per se error-prone in many cases.

Another disadvantage is that in many cases the applied working and auxiliary substances, which are generally used for the marking in the prior art, are applied in liquid form so that a drying time is required after application. In many cases, these drying times of the marking limit the manufacturing speed of the production processes and therefore increase the production costs considerably.

SUMMARY

It is therefore an object of the present invention to provide a marking method which at least substantially avoids the above-described disadvantages of known marking methods. The marking method should allow simple, rapid and reliable marking of defective test elements, and this is intended to be done without significantly increasing the production costs.

The invention provides a marking method for marking defective test elements, a production method which involves this marking method, a marking device for marking defective test elements, a production device for producing test elements while employing a marking device, and an analytical test instrument which uses test elements produced by the method according to the invention. Advantageous refinements of the invention are presented in the dependent claims. These refinements may be implemented individually or in combination with one another.

The test elements are adapted to detect at least one analyte in a sample. They may for example be test elements of the above-described types known from the prior art, for example test elements for the detection of metabolites in liquid samples, particularly in blood, urine, interstitial fat tissue or other bodily fluids. Test elements may however also be used for other types of analytes and samples. The test elements may for example be configured in strip form, in leaflet form, in disc form, in the form of bands or in similar configurations, in each case individually or several combined together. The test elements may be suitable for one or more tests, and they may in particular have one or more test fields onto which the sample can be applied, or into contact with which the sample can be brought.

Like known methods from the prior art, the marking method is configured so that at least some of the test elements are provided with a defect marking which contains information about defectiveness of the test elements. For example, a test element identified as defective may be provided with a corresponding marking.

In contrast to the prior art, in which for example colored marking is carried out, the test elements comprise at least one radiation-sensitive material. In order to be marked, the test elements are exposed to at least one radiation which is adapted and/or selected to induce marking in the form of at least one optically detectable change in the radiation-sensitive material.

In contrast to the prior art, application of an additional marking substance onto the test element is thus not necessary; rather, preferably radiation-sensitive properties of the test element itself are used in order to mark the test element. As an alternative or in addition, markings independent of the functionality of the test elements, in particular a test chemical in test fields of the test elements, may also be applied onto the test elements, for example onto a support band of the test elements or onto separate marking fields independent of the test fields. The marking may be carried out contactlessly so that it does not affect production of the test elements (for example in the form of mechanical contact). It is thus possible to avoid affecting essential machine parameters, for example tension forces on a test element band, as may occur for example when liquid marking means are being applied. Furthermore, the application of a reject marking by means of radiation is virtually independent of the manufacturing speed, so that this is an extremely robust marking process. The marking is generally only a question of the irradiation dose.

Furthermore, besides the material costs for additional marking substances, the marking method according to the invention also obviates the costs of their provision, storage and release. Also, it is generally not necessary to determine by elaborate confirmation tests whether there is an interaction of the marking substances with unmarked test elements. It likewise obviates a strategic dependency on the delivery reliability of particular marking substances.

The said advantages become clear in particular when radiation-sensitive properties of a test material of the test element itself are used. As described above, many types of test elements contain such test materials, which are often also referred to as a "detection chemical" or "test chemical" and which are selected and adapted to change at least one measurable property when the at least one analyte is present in the sample, in particular a measurable electrical and/or optical property. In this regard, reference may be made to the test elements known from the prior art and the test chemical used therein, which is for example applied onto test fields of the test elements.

This detection chemical, or this test material, itself generally has radiation-sensitive properties. This is the case in particular when using optical test elements in which the at least one analyte is detected for example in the form of a color change or a fluorescence change. Detectable, long-term changes in the test materials may however also be induced with other types of test materials by suitable selection of the radiation.

It is particularly preferred for the detectable changes to be configured so that they are irreversible. At least, however, the detectable change should have a stability in the range of a few minutes, preferably from a few hours up to a few days. If the marking remains on the test elements, for example for subsequent readout by a correspondingly adapted analysis instrument, even longer stabilization is necessary, for example an optically detectable change which is stable over a period of from several months to years.

In the case in which the test material of the test elements is itself used as a radiation-sensitive material and therefore to store information about possible defects, application of additional substances onto the test elements for marking can be entirely obviated. This makes the advantages explained above (avoiding the need to check compatibility, cost reductions etc.) particularly clearly beneficial.

As described above, for marking the test elements, as an alternative or in addition to using the test materials or the test chemical which defines the analytical functionality of the test fields of the test elements, a marking may also be applied outside the test fields onto the test elements. To this end, for example, a support material (for example a support band) of the test elements may itself contain a radiation-sensitive material which can be used for the marking. As an alternative or in addition, a separate marking material independent of the test materials or the test chemical and with radiation-sensitive properties may also be applied onto the test elements. For example, separate marking fields may be provided which contain a radiation-sensitive material and which can therefore be marked. Any desired combinations may also be envisaged, for example marking on the test field (in which case the test field has a first radiation-sensitive material) and marking on a separate marking field (which has a second radiation-sensitive material). Accordingly, the invention also provides a test element which is suitable for use in such a marking method and which has at least one such marking field separate from the test field or fields and with a radiation-sensitive material. Here, "separate" is intended to mean a functional separation but not necessarily a strict spatial separation. For example marking fields may be adjacent to test fields, partially overlap with them or even be stacked in a layer structure (for example below the test fields) so that overall the functionality of the test fields is not affected by the marking fields.

The at least one optically detectable change in the radiation-sensitive material, whether pertaining only to the test fields themselves or to separate marking fields, can subsequently be recorded by a suitable sensor and interpreted as a reject marking. Possible configurations of this recording will be discussed in more detail below.

It should be pointed out that it is not categorically necessary to mark the defective test elements with radiation; rather, "inverse" marking by means of the described optically detectable change is also possible. For example, each test element which is identified as defect-free may be marked by means of the radiation whereas each test element identified as defective remains unmarked. Intermediate stages or other types of defect marking are also possible, for example by "writing" information about a quality level of the test element into the radiation-sensitive material using the at least one radiation, for example in the form of a bit value. The information content of the defect marking may thus be configured differently and may in various ways contain information about defectiveness (which may also include freedom from defects) of the respective marked test element (and/or even the test elements, i.e. for example other test elements from a batch). As described above, this may for example involve the information "defective", "not defective", a quality level or similar information. This information about the defectiveness of the respective marked test element is introduced into the radiation-sensitive material by means of the at least one radiation.

It is particularly preferred for the radiation being used, which could in principle also be particle radiation, for example neutron radiation, to comprise electromagnetic radiation. The use of ultraviolet radiation has in particular been found to be expedient, i.e. radiation in the wavelength range between 1 nm and 400 nm. The wavelength range of from 250 nm to 400 nm is particularly preferred, in particular the wavelength range between 350 nm and 380 nm, since this wavelength range not only coincides well with the sensitivity of conventional test materials but is also readily achievable technically. The preferred use of UV light, particularly in the said preferred wavelength range, is therefore advantageous especially in conjunction with the use of a wet chemical as an information medium for the defect information, since many of these test materials or wet chemicals react sensitively to UV radiation, in particular for optical analyte detection. For example, multiple bonds in organic constituents of the test materials may be permanently broken by UV radiation, which may in turn be recognizable for example by a color transformation or another optically detectable change.

Incandescent lamps, gas discharge lamps, lasers, light-emitting diodes, flash lamps or a combination of such light sources, which preferably in turn emit at least partially in the ultraviolet spectral range, may preferably be used in order to generate the at least one radiation.

The optically detectable change, according to the description above, may for example comprise a color change, a change of luminescence (for example fluorescence and/or phosphorescence), a change of reflectivity or a combination of these changes and/or further changes.

The proposed marking method may for example be used as a "stand-alone" method to mark test elements which have already been fully produced. It is particularly preferred, however, to integrate the proposed marking method in one of the proposed embodiments in the scope of a production method for producing test elements of the described type. A multiplicity of the test elements are produced in this production method, and at least one of the test elements (preferably all the test elements and/or random samples of the test elements being produced) is subjected to a defect check.

For example, as explained above, this defect check may involve an optical check (for example a color and/or fluorescence measurement), a visual check (for example in the scope of pattern recognition, in particular by means of a digital image processing program), a fluorescence check or similar types of defect checks or combinations of defect checks. In this way, for example, it is possible to identify whether the test elements themselves (for example a support band of the test elements) are deformed, or whether a detection chemical has been applied correctly (for example whether a test field has been applied and/or whether this test field has been deformed during the application) or the like. Another example of a test criterion for the defect check is represented by the homogeneity of the test fields. For example, it is possible to check whether a test chemical is contained homogeneously and/or with a constant layer thickness on the test field. This homogeneity may for example be checked by means of optical inspection in the visible, infrared or ultraviolet spectral range. As an alternative or in addition, a layer thickness and/or homogeneity inspection may also be carried out for example by means of ellipsometric methods, transmission methods, mechanical sampling methods or other customary layer thickness measurement methods, which can preferably sample or simultaneously record a surface. Thus, for example, defects in the production of the test fields may be found (for example defects in a printing method). Tolerance thresholds for the homogeneity may be specified in this case (for example "allowed" ranges for the layer thickness values inside a test field) in order to qualify the test fields or test elements as defect-free or defective. Another example of a test criterion for the defect inspection is a distance inspection in which (for example optically, for example by means of pattern recognition) spacings of particular elements on and/or in the test elements are compared with threshold values. For example, it is possible to check whether test fields have a predetermined distance from one another and/or a predetermined distance from particular markings. Two- or three-dimensional distance monitoring is also possible. Furthermore tolerance ranges may also be specified, inside which the distance measurements are still tolerable and outside which the test elements are identified as defective. Furthermore, as an alternative or in addition, electrical or electrochemical measurement methods may also be used, for example resistance measurements, impedance measurements or similar types of measurements. A combination of the said defect check types and/or other types of defect check may be used and are known to the person skilled in the art.

The defect check may already be carried out during production of the test elements, so that it may for example be integrated into a manufacturing line. As an alternative or in addition, the defect check may also be done after production.

Conventional methods known to the person skilled in the art may be used for producing the test elements, for example thick film methods, semiconductor technology methods, printing methods or a combination of these/or other customary method steps. The production of the test elements is known to the person skilled in the art. In particular, a band method may be used, as mentioned in more detail below. Furthermore, the test material may preferably be produced separately and subsequently applied onto the band or another type of support (for example in a laminating process).

During or after the defect check, a decision is made as to whether the test element is defective. Similarly as in the description above of the term "defect information" or "defect marking", the term "defective" is to be interpreted in the broad sense. For example, it may involve "digital" defectiveness, for example in the form of defectiveness or freedom from defects (in which case tolerance thresholds may also respectively be specified, for example thresholds for tolerable defects), or a number of intermediate information items. This intermediate information may for example in turn comprise quality grades of the respectively checked test element, which may for example again be expressed in a bit value.

Subsequent to the defect checks or already during the defect check, the test element may in turn be provided with a defect marking which contains information about defectiveness of the respective test element. With respect to this information about the defectiveness, reference may be made to the description above. For this marking of the at least one of the test elements, a marking method according to the above description is used in one of the embodiments presented.

For example, as described above, at least one test material (test chemical) of the test element may in turn be used as an information medium for the marking. For example, as likewise explained above, the marking method may be configured so that the detection chemical or test chemical becomes colored accordingly. In this way, in particular, a test element or a part of the test element (for example a particular test field) may be rendered unusable so that a false measurement value can be excluded from the analyte detection.

This at least one information item, which is contained in the defect marking, may subsequently be used further. In particular, test elements marked in a rejection step may be rejected. This is naturally advantageous particularly for production methods in which test elements are divided up during or after production, so that test elements marked as being defective (i.e. depending on the type of defect information applied, marked or unmarked test elements or test elements which indicate defect information with an insufficient quality level) can be rejected and for example disposed of. For example, a plurality of test elements may be produced as bandware on a common support band, in which case the bandware may for example subsequently be held in a band cassette. Test elements identified as defective may for example be cut out before reception in the band cassette, and the remaining defect-free band may subsequently be reassembled in a splicing step. In this way, defective test elements can be avoided even in bandware. As an alternative or in addition, the bandware may also subsequently be divided up, so that defective test elements can be rejected. In this way, it is respectively possible to ensure that substantially all test elements entering the market are defect-free.

The bandware may also be configured so that (as explained in the introduction for the description of the prior art) it is held in a band cassette. The test band may in this case contain a multiplicity of test elements which, for example, can be used in succession. For example, defective elements may be specially marked so that either they cannot be used, they are identified as defective by an analysis instrument or they are otherwise restricted in their use. As an alternative or in addition, however, it is preferred to assemble the band so that it does not comprise any defective test elements, for example by the above-described cutting process with subsequent rejection and splicing of the remaining band.

The production method may furthermore preferably be configured so that it optionally comprises an inspection step after the at least one method step in which the at least one defect marking is applied. In this inspection step, it is possible to check whether the defect marking has been applied correctly. For example, this may be done by monitoring the at least one optically detectable change in the radiation-sensitive material and comparing it with a setpoint value. For example, this setpoint value may be stored in a data memory, for example a data memory (for example a shift register) which is also used for the defect marking itself. In this way, it is possible to check directly whether the defect marking has been carried out correctly. If it found that this is not the case, then for example a warning may be sent to a technician and/or the defectively marked test element may be marked again and/or rejected. Various other possibilities may be envisaged.

Corresponding to the marking method presented above and the production method respectively in one of the described embodiments, the invention furthermore provides a marking device for marking defective test elements. The marking device may in particular be adapted to carry out a marking method of the described type in one of the alternative embodiments. Accordingly, the marking device has at least one radiation source for exposing the test elements to at least one radiation. For the effect of this radiation and the possible types of marking in the marking device, reference may be made to the description above.

The marking device may furthermore comprise at least one test device, which is adapted to subject at least one of the test elements to a defect test. Preferably all the test elements or random samples of the test elements are subjected to this defect check. With respect to the possible configuration of the defect check, reference may likewise be made to the description above. The marking method is adapted to identify and/or decide whether the test element is defective. With respect to the term "defective" and its possible meanings, reference may likewise be made to the description above.

According to the above description of the possible marking methods, the radiation source may in turn have for example incandescent lamps, gas discharge lamps, lasers, light-emitting diodes, flash lamps or combinations of these and/or other radiation sources, in particular for generating ultraviolet radiation according to the description above and in the preferred wavelength range described above. It is particularly preferred to achieve high parallelity and therefore a high throughput of the marking method, when the marking device has a multiplicity of modularly constructed light sources. In particular, these may be a multiplicity of modularly constructed light generator units for generating ultraviolet light. These modularly constructed light generator units may for example comprise a multiplicity of identical light generator units, which may be arranged for example in a circuitry compartment of the marking device. For example, the circuitry compartment may receive these light generator units in the form of identical slot-in racks.

The marking device may comprise at least one application position where some or all of the test elements are provided with the defect marking. In order to achieve a high level of parallelization and therefore a high throughput, a plurality of application positions may also be provided. For example, a test material (test chemical, detection chemical) in the form of one or more test fields may be applied respectively onto a test element, in which case a separate application position may be provided for each test field.

It is particularly preferred for the marking device to furthermore have at least one waveguide, which is adapted to conduct the radiation from the at least one radiation source to the application position. Depending on the type of radiation being used, this at least one waveguide may in particular be a light waveguide. If ultraviolet light is used as the radiation, which is particularly preferred, then this light waveguide should be matched to the wavelength respectively being used. Rigid or flexible waveguides may be used, for example waveguides with a plastic and/or glass material. Such waveguides may for example be produced as rigid plastic waveguides. It is particularly preferred, however, for the waveguide to comprise at least one fiber light guide i.e. a flexible light guide. Glass fibers and/or, as is particularly preferred, plastic fiber light guides may be used. Respectively, depending on the desired properties of the radiation, multimode or single-mode fibers may be used.

For example a plurality of fiber light guides, for example plastic fiber light guides, may be combined to form fiber bundles. For example, the preferred UV light generator units described above, which are preferably located in a circuitry compartment of the marking device, may be connected to the at least one application position via one or more fiber bundles.

If fiber bundles are used, then it is in particular preferred for the marking device to comprise at least one cross-section converter. This cross-section converter is adapted to hold a multiplicity of fiber light guides of at least one of the fiber bundles so that the fiber ends of the fiber light guides are arranged in a predetermined pattern in the application position. In this way, for example by corresponding arrangement of the fiber ends to form a pattern, the throughput of the test elements can be increased since a plurality of test elements can be exposed in parallel, intensities and radiation doses can be increased (by simultaneous exposure using a plurality of fibers and/or exposure using a plurality of fibers in succession), and a plurality of defect markings could even be written simultaneously onto an individual test element.

This configuration of the marking device becomes clearly advantageous in particular when, as is likewise preferred, the test elements are produced in a continuous process. For example, the test elements could be produced in the form of a continuous test element band which, as described above, is subsequently divided up or which may be held as a whole or in sections in a band cassette. The pattern of the fiber ends which is generated by the cross-section converter may in this case permit simultaneous irradiation in the application position both, for example, parallel to a running direction of the band and, as an alternative or in addition, perpendicularly to the running direction of the band. A plurality of bands may also be processed simultaneously, for example by a plurality of bands with test elements being generated in parallel. For example, when producing bandware, a wide band may initially be produced with a plurality of test elements respectively arranged in parallel, which is then cut up into a plurality of sub-bands (for example in a cutting process).

The marking device may have a guide table in the application position, in which at least two, preferably at least five test elements can be exposed simultaneously to the radiation i.e. marked. For example, five bands or sub-bands with test elements may be passed simultaneously through the guide table.

For the predetermined pattern which is produced by the cross-section converter, in particular a line pattern (for example with a line parallel and/or perpendicular to the movement direction of the band), a matrix pattern or a rectangular pattern is preferred. Other patterns are of course also possible. It is also possible to arrange a plurality of cross-section converters in parallel with one another, for example a plurality of cross-section converters with fiber ends respectively arranged linearly. This is advantageous particularly in the above-described alternative embodiment in which a plurality of test bands with test elements are produced in parallel, since in this way for example a cross-section converter with a fiber end pattern can be assigned to each band or sub-band.

As an alternative or in addition, the marking device may furthermore have at least one set of beam shaping optics for beam shaping of the radiation. For example, lens systems may be provided in order to bring the markings or the shape of the markings on the test elements into a desired shape, for example a linear or rectangle shape.

Besides the marking device, the invention furthermore provides a production device for producing test elements which may in particular be adapted to produce test elements according to the above-described production method in one of the described method variants. The production device has a fabrication device for producing a multiplicity of test elements. As described above, production devices known from the prior art may for example be used for this fabrication device, for example production devices which operate with semiconductor and/or thick film processes and/or printing methods and/or adhesive bonding methods. In particular, the production device may be adapted to produce a multiplicity of test elements continuously, for example in the form of a band process, a multiplicity of test elements being held on a band. These test elements may subsequently be divided up, or the band may be used per se, for example in a band cassette.

The production device furthermore has at least one marking device according to one of the embodiments described above. Besides this, the production device may furthermore have at least one sorting device for rejecting test elements marked as being defective. When producing bandware, for example for a band cassette with test elements, it is preferred for the production device furthermore to have a cutting and splicing device i.e. a device which can cut defective test elements out from a band in order subsequently to adhesively bond this band back together or reassemble it in another way, for example by lamination. In this way, an endless band with defect-free test elements can be produced. Again, the terms "defective" and "defect-free" are to be interpreted in the broad sense, for which reference may be made to the description above. For example, tolerance thresholds may again be specified. Depending on whether the test elements are divided up during or after production, instead of being rejected defective elements may also for example stay on a band and merely remain unused subsequently, for example by readout of the marking (see also below).

The production device may in particular furthermore have at least one test device. This test device is adapted to subject the test elements to a defect check. The defect check methods already described above may be used for this, i.e. for example electrical, electrochemical or optical measurements or a combination of these defect check methods. For example, the test device may comprise a camera by which the test elements are recorded. As an alternative or in addition, for example, an image recognition system may also be provided which is for example adapted to detect deviations of a test field and/or a shape of the test elements from a predetermined standard (for example by more than a predetermined tolerance threshold). As an alternative or in addition, one or more test light sources may also be used, for example in order to check fluorescence properties and/or color properties and/or reflection properties of the test element, for example properties of the test chemical and/or of one or more test fields. Furthermore, as an alternative or in addition as likewise explained above, one or more resistance measurement devices may for example also be provided and/or one or more impedance measurement devices and/or similar devices for electrical or electrochemical defect checking. The production device, in particular the test device, may as an alternative or in addition furthermore comprise one or more data memories, which may be volatile and/or nonvolatile data memories. In the scope of mass production, it is particularly preferred for this at least one data memory to comprise at least one shift register. For example, a continuous or stepwise production process may in turn be used, in which the defect check takes place at one site by means of the defect checking device, in which case the results of this defect check may be entered into the data memory, in particular the shift register. In this way, a multiplicity of test elements can be tested in succession so that a test element currently located in the marking device (for example one or more test elements in an application position) can respectively be assigned to the information item or items by corresponding readout of the shift register, for example of the marking device. In this way, the test elements can be marked by means of the marking device. Similarly, the information may also be used subsequently for rejection of the test elements.

Similarly as the description above of a preferred method in which an inspection step is carried out, the production device may furthermore comprise at least one inspection device which is adapted to check whether marking has been carried out correctly in the marking device. For example, the inspection device may in turn receive data from a data memory, for example a shift register, preferably using the same data as that which the marking device can access and on the basis of which the defect markings of the test elements have been applied. In this way, by cross-referencing, it is possible to ensure at least substantially that the marking device is operating correctly and for example failures in individual light sources or other types of malfunctions can be identified. If such a malfunction is identified, then for example the production device may be configured so that it rejects the defectively marked test elements and/or sends a warning to a technician or carries out similar actions. The inspection device may for example comprise one or more photodiodes and/or other types of photodetectors, in order to monitor the at least one optically detectable change in the radiation-sensitive material. One or more light sources may also be provided, for example in order to assist function of the photodetectors by corresponding exposure of the radiation-sensitive material.

The invention furthermore provides an analytical test instrument for detecting at least one analyte in a sample, which comprises at least one test element that is produced by the production method described above in one of the method variants presented. As a counterpart to the defect marking which may be present on the test element, the analytical test instrument has an interrogation device which is configured to identify whether the test element is marked. To this end, the interrogation device is adapted to identify the at least one optically detectable change in the radiation-sensitive material of the test element.

For example, this analytical test instrument may furthermore comprise a drive and evaluation device for carrying out a quantitative and/or qualitative detection of the at least one analyte in the sample by means of the at least one test element. It is particularly preferred for the analytical test instrument to be adapted to determine a blood sugar concentration. In this case, it is possible to use individual test elements, a plurality of test elements which are held in a magazine (in which case for example a test element is respectively taken from the magazine), or test elements which are held in a band cassette. Other types of test elements are also possible, for example implantable test elements.

The interrogation device is therefore configured to interrogate the defect marking of the at least one test element, preferably the at least one test element which is currently being used or intended to be used. If, according to the information contained in the defect marking, it is found that the test element is defective, then various actions may be carried out. Inter alia, a warning may be sent to a user of the analytical test instrument, for example via a display, optical indicator elements (for example warning lights), via acoustical signals or via a combination of these options. As an alternative or in addition, a test with the marked test element may also be prevented. Furthermore, as an alternative or in addition, it may be required that a new test element should be taken from a multiplicity of test elements held in a magazine. For example, as explained above, said test elements in said magazine may be individual test elements or flexibly or rigidly connected test elements. A band cassette may for example also be used, so that it is possible for example to wind forward to a subsequent test field in the event that a test field is identified as defective.

Further details and features of the invention may be found in the following description of preferred exemplary embodiments in conjunction with the dependent claims. The respective features may be implemented on their own, or several may be implemented in combination with one another. The invention is not restricted to the exemplary embodiments. The exemplary embodiments are represented schematically in the figures. Reference numerals which are the same in the figures denote elements which are identical or functionally equivalent, or which correspond to one another in respect of their function.

DETAILED DESCRIPTION OF THE ILLUSTRATED EMBODIMENTS

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
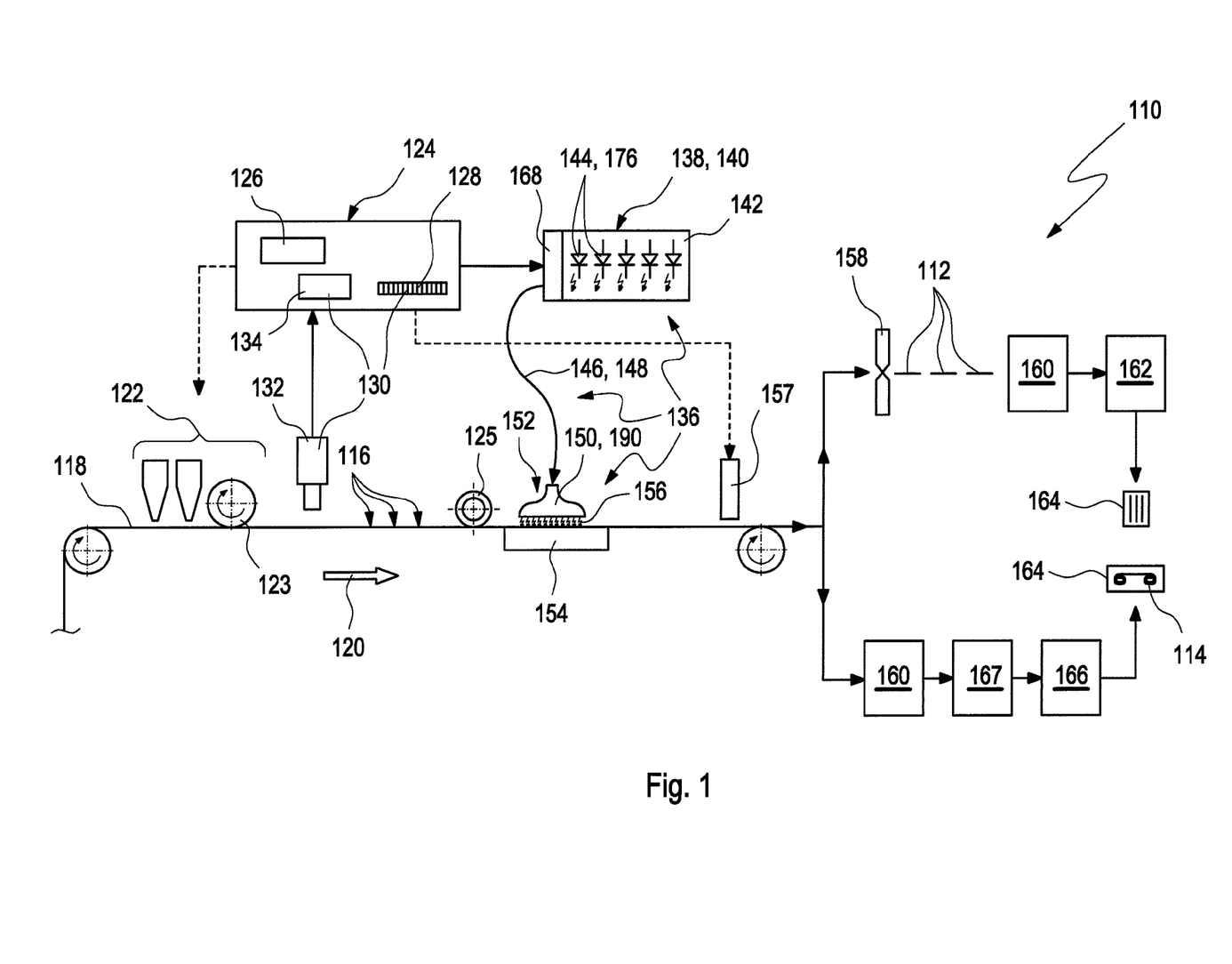
FIG. 1 shows a schematic structure of an exemplary embodiment of a production device according to the invention with the marking device.

FIG. 1 represents an exemplary embodiment of a production device 110 for the production of the test elements for detecting at least one analyte in a sample. The test elements are denoted by the reference numerals 112, 114 and 116 in FIG. 1, depending on the production state or stage which these test elements occupy inside the production device 110, or depending on the configuration of these test elements.

The individual elements of the production device 110 are arranged merely symbolically in FIG. 1. A continuous production process is represented, in which the test elements are initially produced as a bandware 116 on an endless band 118. For example, this endless band 118 may be a paper band, in particular a multilayered coated paper band. Other support materials may also be used as an alternative or in addition, for example plastic bands, ceramic bands, composite materials and similar support materials. For example a polyethylene sheet, a PET sheet or another sheet material may be used as a support material. The production direction from the starting material to the finished test elements 112, 114 passes from left to right in FIG. 1, which is symbolically represented by the arrow 120 in FIG. 1. As an alternative to continuous production processes as represented in FIG. 1, discontinuous processes are also possible, for example batch processes, in which test elements are produced individually or in batches. This may also be done in the case of band-type products, for example by winding sections of bandware onto support rolls in order to be temporarily stored and/or transferred to other method sections. The production process may also be interrupted so that, for example, the test elements can be manufactured at different sites (for example at different stations) in various manufacturing stages. Furthermore, the sequence of the individual process steps of the production process of the production device 110 as represented is not categorically necessary, i.e. for example testing and marking of semifinished test elements may also be carried out so that for example further production steps may follow testing and marking.

The production device 110 has a fabrication device 122, which is indicated merely symbolically in FIG. 1. Here, for example, the endless band 118 may be provided with test fields where a test material (also referred to below as a test chemical or detection chemical) may respectively be applied onto the endless band 118. The application may for example be carried out by adhesive bonding, which is indicated symbolically by an adhesive bonding station 123 in FIG. 1. Here, for example by an adhesive bonding or a laminating process, test fields with the test material (test chemical, detection chemical) may respectively be bonded adhesively onto the support material. Besides the test material, markings which are used for subsequent positioning of the test elements 116 in an analytical test instrument may furthermore be applied, for example printed, onto the support band 118 as well.

The fabrication device 122 may comprise various individual devices for producing the test elements 116, for example coating nozzles, printers (for example screen, template, pad, inkjet or flexographic printers) or other types of fabrication apparatus or combinations of fabrication apparatus. A plurality of bands may also be combined as support materials. It is also possible to subdivide the fabrication partially into separate methods, so that for example semifinished products such as a printed support band may be delivered to the fabrication device 122. The apparatus of the fabrication apparatus 122, which are known to the person skilled in the art from the production of test elements, need not be discussed in further detail.

It is particularly preferred for the fabrication apparatus 122 to be adapted so that it produces a wide support band 118 on which a plurality of test elements 116 are arranged in parallel with one another. For example, the band 118 may initially be configured so that five such test element tracks are arranged next to one another. These may then be cut into individual test element bands, for example by longitudinal cuts in a cutting device (symbolically denoted by 125 in FIG. 1). This cutting may be carried out at various stages of the production process shown in FIG. 1. A different configuration is nevertheless also possible, i.e. for example a configuration with merely one support band 118.

The production device 110 in this exemplary embodiment furthermore has a central control unit 124. Likewise, as an alternative, this control unit 124 may also be constructed decentrally so that the production device 110 may for example comprise a plurality of controllers. These controllers may be connected to one another, or they may also operate autonomously. In this exemplary embodiment, the central control unit 124 comprises at least one processor 126 and at least one data memory 128. This at least one data memory 128 may in particular comprise a shift register. The central control unit 124 may for example be configured in program technology in order to control a production method, for example a production method according to one of the exemplary embodiments described above.

The production device 110 furthermore comprises one or more test devices 130. This test device 130 is also represented merely symbolically in FIG. 1. For example, this test device 130 may comprise one or more cameras 132. These cameras may for example be configured to observe the test fields on the test elements 116, which are for example still configured as bandware at this production stage. The test device 130 may furthermore comprise an image recognition system 134, which may for example be designed decentrally or (as symbolically represented in FIG. 1) as a component of the central control unit 124. The image recognition system 134 may in particular comprise one or more image recognition software modules, which may for example run on the at least one processor 126. The image recognition system 134 may be adapted to evaluate image data, which are generated by the camera 132. In this way, for example, it is possible to identify when test fields of the test elements 116 deviate from a predetermined form, for example in respect of their shape and/or color. In this way, for example, defects which have occurred in the fabrication device 122 can be identified. Other types of defects may in principle also be detected, as well as other types of test devices 130, for example transmission measurements, reflection measurements, fluorescence measurements, resistance measurements, impedance measurements or combinations of these and/or other measurements.

The test device 130 and/or the central control unit 124 may for example be configured so that information is assigned to each individual test field of the test elements 116. In the simplest case, this information may be a 1-bit value which is for example entered for each individual test field into a shift register of the data memory 128. In this way, the information travels virtually with the test elements in the throughput direction 120. Other types of information allocation may nevertheless also be envisaged. It will be assumed below that a 1-bit defect information value is stored, in which for example "0" stands for "defect-free" and "1" stands for "defective". As described in detail above, other configurations of the defect information are nevertheless also possible.

After the test device 130 in FIG. 1, the test elements 116 pass through a marking device 136 which is likewise represented merely symbolically in FIG. 1. According to the result of the defect check in the test device 130 as described above and the defect information for example correspondingly stored in the data memory 128 for each test element 116 and/or for each test field of the test elements 116, the test elements 116 are marked in this marking device 136. The marking is configured in particular so that the defect information can be reconstructed from it. For example, it is possible to mark each test element 116 as a whole and/or each test field of the test elements 116 individually. It will be assumed below that the marking is carried out so that defective test fields are marked whereas defect-free test fields and/or defect-free test elements 116 remained unmarked. In the present exemplary embodiment, it is assumed that the test materials of the test elements (i.e. the test chemical of the individual test fields of the test elements) is itself used as an information medium, i.e. as a radiation-sensitive material. This will be explained in more detail below.

The marking device 136 has a radiation source 138 in the form of a light generator unit 140. This light generator unit 140 is constructed modularly and has for example a circuitry compartment 142 with a power supply in the form of an electrical supply unit 168 and a multiplicity of modular individual light sources 144. These individual light sources 144 are represented symbolically as light-emitting diodes in, FIG. 1, UV light-emitting diodes preferably being used.

Figure 2:
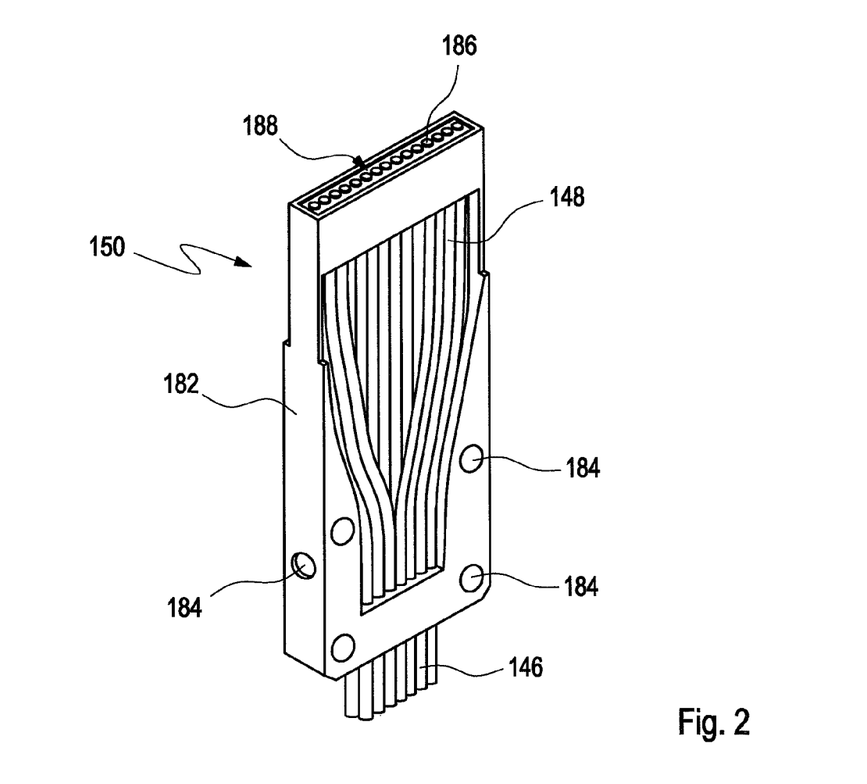
FIG. 2 shows an exemplary embodiment of a cross-section converter.

The radiation source 138 in this exemplary embodiment is preferably connected via a fiber bundle 146 with a multiplicity of plastic fiber light guides 148 to at least one cross-section converter 150. This at least one cross-section converter 150, which will be explained in more detail below with the aid of FIG. 2, is arranged in an application position 152 preferably above the test elements 116. The test elements 116 are preferably guided in this application position in a guide table 154, in which case a plurality of bands (for example five bands after cutting in the cutting device 125) may be guided in parallel through the application position 152. The guide table 154 may in particular ensure that the bands of the test elements 116 are positioned exactly, in particular exactly with respect to the cross-section converter 150. In this way, according to the intended marking of the test elements 116 in the marking device 136, the test elements 116 may be exposed to radiation 156 (which is indicated merely symbolically in FIG. 1). This radiation exposure may in particular be controlled in turn by the central control unit 124, for example according to the information stored in the shift register of the data memory 128 for each individual test element 116 and/or for each individual test field of the test elements 116.

After passing through the application position 152, the test elements 116 may in principle be used. An inspection device 157 is optionally provided in FIG. 1, which inspects whether the markings have been applied correctly in the marking device 136. For example, this inspection device 157 may comprise a separate photodiode or other detector for each band, which checks the markings. This information may for example be evaluated in the central control unit, where for example the identified markings are compared with setpoint information stored in the data memory 128, particularly in the shift register. If a defect marking is found in this case, then for example a warning may be sent or the respective test element 116 may be rejected.

Furthermore, the test elements 116 may optionally also be subjected to other processing steps, for example further at least partial coating, application of protective materials or the like. As described above, to this end for example further fabrication devices 122 may follow downstream of the application position 152 in the throughput direction 120.

As described in the introduction, there are many different embodiments of test elements. In FIG. 1, therefore, two possibilities in the form of a "branch" are represented symbolically and merely generically for the numerous different possibilities for the configuration of test elements which may be used in the scope of the present invention. Thus the bandware of the test elements 116 as a "precursor" may be divided up into individual test elements 112 for example in a dividing device 158 which is likewise represented merely symbolically in FIG. 1. This dividing device may be followed by a sorting device 160, in which the divided test elements 112 can be separated into defect-free and defective elements according to their marking applied in the application position 152. As described above, however, sorting into a plurality of classes may also be carried out instead of purely digital sorting. The sorting device 160 may then be followed by a packaging device 162 in which the test elements 112 are for example cassetted, magazined and/or provided with repackaging and/or blister packaging. As represented symbolically in FIG. 1, this results in the finished test element containers 164.

As an alternative to dividing and producing individual test elements 112, the test elements may also be configured as band-like test elements 114. To this end, for example, sections of the bandware-type test elements 116 may be cut and processed in a cassetting device 166 to form band cassettes (indicated symbolically in FIG. 1). In order to be able to reject defective test elements (i.e. individual test elements suitable for a single test or test elements suitable for a plurality of tests) from test elements 114 in bandware form as well, the cassetting device 166 may in turn be preceded by a sorting device 160. In this sorting device 160, defect information may in turn be read out from the markings of the individual test elements or test element sections (i.e. sections which are respectively suitable for a single test). If it is found that a test element 114 or a section of this test element 114 is defective, then this section may for example be cut out. So that a continuous band can nevertheless subsequently be cassetted, the sorting device 160 may correspondingly be assigned a cutting and splicing device 167, which is arranged downstream of the sorting device 160 in FIG. 1. Other arrangements are however also possible, for example arrangements in which the cutting and splicing device 167 is a component of the sorting device 160. In the cutting and splicing device 167, band sections which are marked as being defective are cut out, removed and the ends of the remaining band are reconnected ("splicing"), for example by adhesive bonding. This technique is known for example from traditional cinema film technology.

In this context, in view of the many different possibilities for the technical configuration of test elements, it should be pointed out that the term "test element" is to be interpreted in the broad sense in the scope of the entire invention. They may be elements which have at least one test field that is suitable for the qualitative or quantitative detection of the at least one analyte. For example, a single strip-shaped test element 112 with a single test field or a plurality of test fields may be used as the test element. For example, a plurality of test elements may respectively be provided for a particular analyte. As an alternative, as likewise explained above, bandware may also be used as test elements so that in this case band-like test elements 114 are provided. In this case, the entire test element bands of the band-like test elements 114 may be referred to as a test element, or individual test sections on these band-like test elements 114, for example test elements respectively with a test field, may be referred to as a test element. Without restriction of the possible other meanings and different nomenclature, the latter will be assumed below so that an individual test section for a test will be referred to as the test element 114 in the case of bandware.

The light generator units 140 of the marking device 136, or the modularly constructed individual light sources 144, may in particular be configured so that a plurality of individual light sources 144 are combined in a circuitry compartment 142, one electrical supply unit 168 respectively being assigned five individual light sources 144 in a row in this exemplary embodiment.

The individual light sources 144 are for example respectively enclosed by a slot-in housing which allows insertion into the circuitry compartment 142. A plug connector, via which the modular individual light sources 144 can be supplied with energy, may respectively be provided on the rear side of the slot-in housing. Data interchange may furthermore take place via these plug connectors, so that for example the individual light sources 144 (or individual radiation sources contained in these individual light sources 144) can be driven appropriately in order to control the marking in the marking device 136 expediently. For example, this control may in turn be carried out via a central control unit 124.

The individual light sources 144 may respectively contain electronics boards which, for example, may comprise one or more printed circuit boards fitted with components. A multiplicity of light-emitting diodes, in particular UV light-emitting diodes 176, which can preferably be driven individually, may respectively be contained on these electronics boards. These UV light-emitting diodes 176 may preferably be light-emitting diodes with a wavelength in the range of about 250 nm to 400 nm, particularly in the range between 350 and 380 nm, which preferably have a power of from 50 mW to 500 mW, particularly preferably in the range of 100 mW to 200 mW. To this extent, the expression "individual light source" 144 is not to be understood as meaning that these individual light sources 144 respectively comprise only a single radiation source; rather, a plurality of radiation sources may be provided in the form of UV light-emitting diodes 176, as in this exemplary embodiment.

A number of UV light-emitting diodes 176 equal to five may for example be provided per electronics board. For light guiding, for example, a coupling plate in which individual plastic fiber light guides 148 are fixed with their input ends, may be arranged above the UV light-emitting diodes 176. This fixing may for example be carried out by adhesive bonding, by clamping or by a combination of fixing techniques. Other techniques are also possible. The fixing is carried out such that one input end of the plastic fiber light guides 148 is respectively arranged above one UV light-emitting diode 176, so that the light of this UV light-emitting diode 176 is respectively input into one plastic fiber light guide 148. This simple allocation is generally sufficient for the input, although more complex input optics may also be provided, for example lens systems, in particular microlens systems, or similar input devices.

The plastic fiber light guides 148 are subsequently combined to form fiber bundles 146, which may for example be fed out from the slot-in housing of the individual light sources 144 via strain relief devices. A plurality of the fiber bundles 146 may subsequently be assembled to form higher-level fiber bundles 146, for example in order to be guided as a common fiber bundle 146 to the application position 152 in FIG. 1 (in which case a plurality of application positions 152 may also be provided as appropriate).

FIG. 2 shows a possible exemplary embodiment of a cross-section converter 150 in perspective representation. The cross-section converter 150 comprises a frame 182, in which for example a multiplicity of openings 184 may be provided, which may in particular allow pinning, screwing or other fixing of the cross-section converter 150. These openings 184, which may for example be configured as pinning bores or pin bores, are represented merely schematically in FIG. 2 and may also be adapted to the respective pinning situation or other assembly techniques and configured differently. In this way, a plurality of cross-section converters 150 can be combined to form cross-section converter modules, for example by pinning or screwing, and fixed in the application position 152. The frames 182 may for example be made of aluminium, stainless steel, plastic and/or other materials.

The cross-section converters 150 are configured so that they split an incoming fiber bundle 146 (at the bottom in FIG. 2) into individual plastic fiber light guides 148. The output fiber ends of the individual plastic fiber light guides 148 (at the top in FIG. 2) are arranged to form a desired pattern 188 and fixed in this way. Again, this fixing may be carried out by clamping, adhesive bonding or by a type of fixing. In the preferred exemplary embodiment represented in FIG. 2, the pattern 188 has a line pattern in which, in this exemplary embodiment, fifteen fiber ends 186 are arranged preferably at least approximately equidistantly to form a line. Since preferably two or more such cross-section converters 150 are respectively arranged successively in the throughput direction 120 in a module, this respectively gives in total a line pattern with thirty or more fiber ends 186 arranged in a row. Each fiber end 186 may for example have a diameter of about 1 mm to 3 mm. Such a line emits for example in total a UV light power of about 500 mW to 1500 mW, for example about 1000 mW.

As described above other types of patterns 188 may nevertheless also be used, for example matrix patterns with for example a rectangular matrix. Other configurations are also possible. In particular other types of fibers instead of plastic fiber light guides 148 may also be used, for example glass fibers. Also, instead of the simple output from the fiber ends 186 as represented in FIG. 2, additional beam shaping optics may be provided, for example with one or more common lenses for all the fiber ends 186, or with individual lenses for the fiber ends 186. In this way, the beam cross sections can be adapted further.

In the arrangement according to FIG. 1, for example, a plurality of cross-section converters 150 in the application position 152 may be combined to form an application module 190. In this case a plurality of cross-section converters 150 are preferably pinned with pins and/or screwed through the openings 184 represented in FIG. 2. The openings 184 may for example be configured as bores and/or pin bores and/or threaded bores. In particular a clamping frame may be provided in order to receive the individual modules of the cross-section converters 150. In the representation according to FIG. 1, each of the cross-section converters 150 may for example correspond to the exemplary embodiment according to FIG. 2, although the cross-section converters 150 are rotated in comparison with FIG. 2 so that the fiber ends 186 (not visible in FIG. 1) point downwards in FIG. 1. Preferably (not represented in FIG. 1) two such cross-section converters 150 are arranged successively in series in the throughput direction 120, and preferably five such cross-section converter pairs are arranged next to one another perpendicularly to the throughput direction 120.

The guide table 154 represented schematically in FIG. 1 comprises for example five rectangular guide grooves, which are respectively matched in respect of their dimensioning to the bandware of the test elements 116. This dimensioning may for example be configured so that these guide grooves correspond in their width to the individual strips which are obtained after the cutting device 125 (in which wide test strips are for example cut longitudinally into three, five or another number of narrower strips) and are respectively delivered to the guide grooves. Overall positioning of uncut test elements 116 by the guide table 154 is however also possible in principle.

In this way the band-like test elements 116 are guided precisely by the guide table 154 and its guide grooves, so that the test elements 116 or test fields arranged thereon and/or other types of radiation-sensitive materials (for example marking fields) can be positioned exactly with respect to the fiber ends 186. Since for example the shift register of the data memory 128 in FIG. 1 contains information as to which test elements or test fields or marking fields are currently located in the application position 152, the individual light sources 144 or light-emitting diodes 176 contained in them can thereby be switched appropriately in order to mark particular test elements 116 expediently, particular test fields and/or particular marking fields. As an alternative or in addition, here as in other possible embodiments of the invention, positioning marks may also be provided on the test elements 116, which additionally facilitate positioning and/or identification of the test elements 116 for marking.

Figure 3:
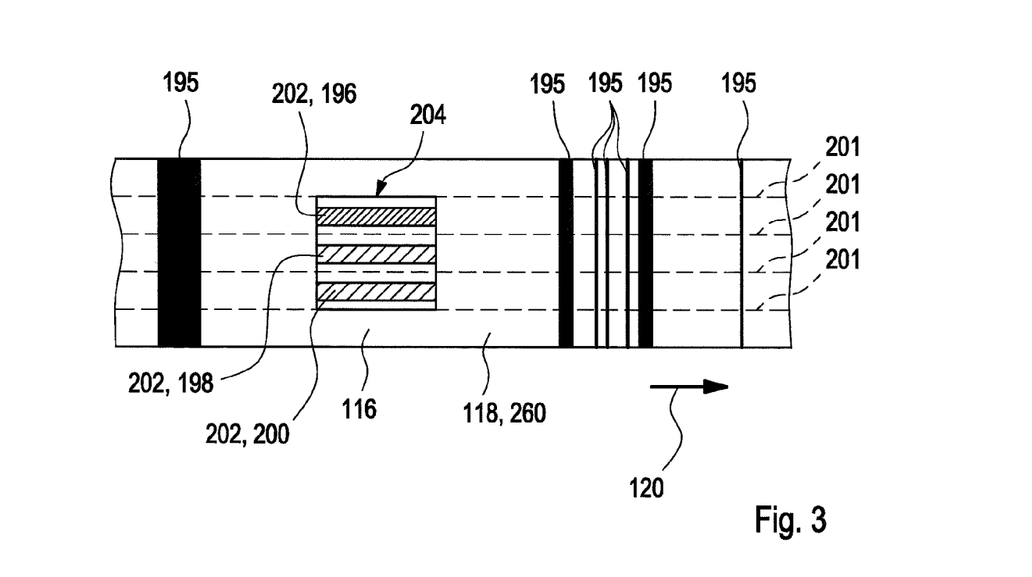
FIG. 3 shows a test element in the form of a band with a plurality of test fields, of which one test field is marked.

FIG. 3 represents an exemplary embodiment of the test element 116. The test element 116 is configured as bandware in this example, merely one test section of the band being shown. The band of the test element 116 in this exemplary embodiment is provided with a multiplicity of positioning marks 195, which are printed onto the endless band 118 for example by a screen printing method. These positioning marks 195 may be used for positioning the bandware during production of the test elements 116, and/or they may be used to position the test elements correctly for sample application and/or evaluation of the test subsequently during use of the test elements 116 in an analysis instrument.

The exemplary embodiment in FIG. 3 shows a test element 116 before it passes through a cutting device 125 (see FIG. 1). This means that in the case represented it is still a wide uncut raw band, in which three individual (in this case rectangular) test fields 196, 198 and 200 are respectively arranged parallel to one another on the endless band 118 and in this state still form an overall test field 204. This uncut band may subsequently also be cut in the cutting device 125, for example along the cutting lines 201 indicated in FIG. 3, so as to finally obtain the actual band-like test elements 116 in which only one of the test fields 196, 198, 200 is respectively arranged adjacently. The edge strips without test fields may be discarded. As an alternative, however, the band represented in FIG. 3 may also be used uncut so that a test element 116 has three test fields 196, 198, 200 next to one another. These could for example be used for averaging.

The test fields 196, 198 and 200 comprise for example a detection chemical which experiences a color transformation when a liquid sample is applied, for example a blood sample, according to the presence of an analyte, for example blood glucose. This detection chemical is employed as a radiation-sensitive material 202 in the present exemplary embodiment, which is used as an information medium for the defect information. As explained above, however, in this or other exemplary embodiments it would also be possible to use separate marking fields which have radiation-sensitive materials independently of the test chemical.

The exemplary embodiment of a test element 116 as represented in FIG. 3 has already passed through the application position 152. The upper test field 196 in FIG. 3 has deliberately been exposed by means of the radiation source 138, which results in a visible color change of this test field 196 relative to the unexposed test fields 198, 200. In this way, for example, the upper test field 196 can deliberately be made unusable for an analysis. The color change may for example be identified photometrically (for example by a reflection, transmission or color measurement or other types of measurements). It should be pointed out that the test element 116 represented in FIG. 3 was therefore not produced in the fabrication device 110 shown in FIG. 1, since the test elements 116 in FIG. 1 are already cut in the cutting device 125 before they reach the marking device 136, in contrast to the uncut and still marked test element 116 in FIG. 3. The example in FIG. 3 serves however merely to illustrate the principle of the invention. Marking after cutting is also possible, similarly as in FIG. 1.

Figure 4:
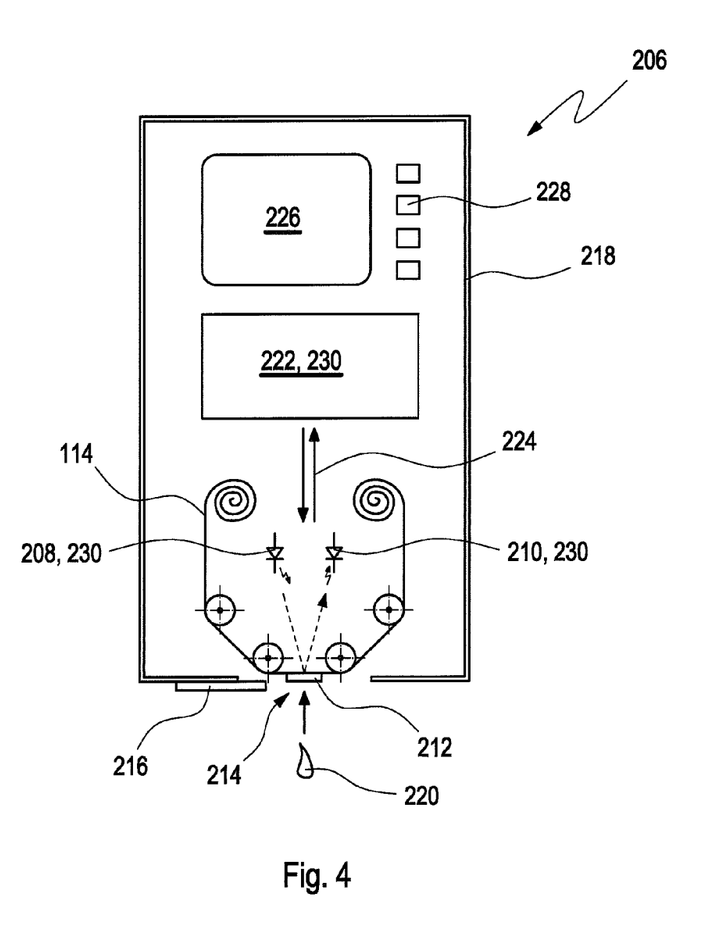
FIG. 4 shows an exemplary embodiment of an analytical test instrument.
Figure 5:
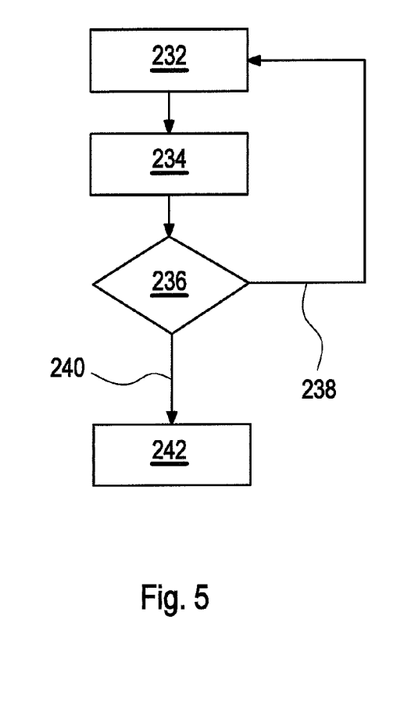
FIG. 5 shows an exemplary embodiment of a method for determining an analyte concentration by means of an analytical test instrument.

FIG. 4 symbolically represents an exemplary embodiment of an analytical test instrument 206 according to the invention, which operates with test elements 114 marked according to the invention. Furthermore, FIG. 5 represents a possible method for detecting at least one analyte in a sample, which may be carried out particularly in conjunction with the analytical test instrument represented in FIG. 4 but which may however also be used independently of it.

It should be pointed out that in the ideal case, which also constitutes the normal case, the test elements 114 are produced so that no test elements 114 marked as being defective enter circulation. To this extent the analytical test instrument 206 described below, or an analytical test instrument 206 according to the invention in another embodiment of the invention, merely provides additional security that if despite rejection of defective test elements 114 during production, such test elements marked 114 as being defective should enter into circulation, they are not used for tests. As an alternative, although this is less preferred, selection could be carried out only at the time of testing by means of the analytical test instrument 206, so that test elements 114 marked as being defective are not rejected until during the testing, i.e. they are not used. This would have the disadvantage that under certain circumstances a smaller number of test elements 114 would be available, although this could be possibly be compensated for by a surplus of test elements 114 (i.e. an extra number in addition to the nominal number of individual test elements 114), particularly in the case of a multiplicity of test elements 114.

In this exemplary embodiment, the analytical test instrument 206 has for example a band-like test element 114, for example a test element 114 held in a band cassette. Other types of test elements could nevertheless also be provided as an alternative or in addition, for example strip-like test elements, for example in a linear magazine, a drum magazine, a disc magazine or another type of magazine.

In this exemplary embodiment, the analytical test instrument 206 has an optical excitation device 208 and an optical detection device 210, which are indicated merely symbolically in FIG. 4. By means of this excitation device 208 which may for example comprise one or more light sources, and the detection device 210 which may for example comprise one or more photodiodes, one or more test fields 212 on the test element may for example be examined for analyte-introduced color changes in a test position 214. The analytical test instrument 206 in this example preferably has a cover 216 in a housing 218 of the analytical test instrument 206. This cover 216 releases the test position 214 or a test field 212 located in this test position 214 for the application of a sample 220, which is preferably a liquid sample in this exemplary embodiment.

The analytical test instrument 206 furthermore has a drive and evaluation unit 222. This drive and evaluation unit 222 may for example comprise one or more microcomputers and be adapted to drive the excitation device 208 and/or the detection device 210. Transport of the band-like test element 114 may furthermore be controlled, so that delivery of a test field 212 into the test position 214 can be controlled. These controls, and data interchange in the other direction, are symbolically indicated by the double arrow 224 in FIG. 4.

The analytical test instrument 206 furthermore preferably has indicator means, for example a display 226, and user interface elements 228. In this way, the functions of the analytical test instrument 206 can be controlled and measurement information can be output.

In normal operation i.e. operation known to the prior art, under the control of the drive and evaluation unit 222 a particular test field 212 is moved into the test position 214, the cover 216 is released and application of the sample 220 is enabled. An optical evaluation of the test field 212 is subsequently carried out by the excitation device 208 and the detection device 210, so that for example an analyte concentration can be determined, in particular a blood sugar concentration. This may for example be output on the display 226.

According to the invention, however, the analytical test instrument 206 in the exemplary embodiment represented in FIG. 4 furthermore has an interrogation device 230 which is adapted to identify and evaluate markings which, for example, have been applied onto the test element 114 and/or the test field 212 according to the method described above. In this exemplary embodiment represented in FIG. 4, this interrogation device 230 uses the excitation device 208 and the detection device 210 as well as a corresponding interrogation algorithm, for example implemented as software technology in the drive and evaluation unit 222. As an alternative, however, the interrogation device 230 could also be implemented as a separate device distinct from the excitation device 208 and the detection device 210, for example by means of a separate interrogation excitation device and/or a separate interrogation detection device (not represented in FIG. 4). Marked test elements 114 and/or marked test fields 212 may be identified in this way, for example by detecting a coloration of the test fields 212.

In the proposed method, a particular test element 114 and/or a particular test field 212 is initially provided in the test position 214. This is denoted symbolically by the reference 232 in FIG. 5. The interrogation device 230 is subsequently used to interrogate whether the test field 212 and/or the test element 114 is provided with a marking, and/or the defect information contained in the marking is read out (step 234). This information may for example be evaluated in the drive and evaluation unit 222. A decision step 236 may subsequently be carried out, in which a decision is made as to whether the test field 212 and/or the test element 114 is defective according to the defect information read out (branch 238) or defect-free (branch 240 in FIG. 5). If the test field 212 and/or the test element 114 is identified as defective, a warning may optionally be sent to the user, for example in the form of a visual warning (for example on the display 226) and/or an acoustic warning. As an alternative or in addition, as represented in FIG. 5, step 232 may be repeated, a new test field 212 and/or test element 114 being provided. In the arrangement according to FIG. 4, for example a fresh previously unused test field 212 may be moved into the test position 214. For example, with the arrangement in FIG. 4, the method steps described so far may be carried out such that the cover 216 is closed while these method steps are being carried out, so that application of the sample 220 is not yet possible.

If however it is found in step 236 that the test field is defect-free, then a measurement 242 may subsequently take place, the detection of at least one analyte in the sample 220 being carried out. For example, in the scope of this measurement in FIG. 4 the cover 216 may be released and/or the excitation device 208 and the detection device 210 may be put into operation, for example in order to carry out an analyte-induced color change.

Figure 6:
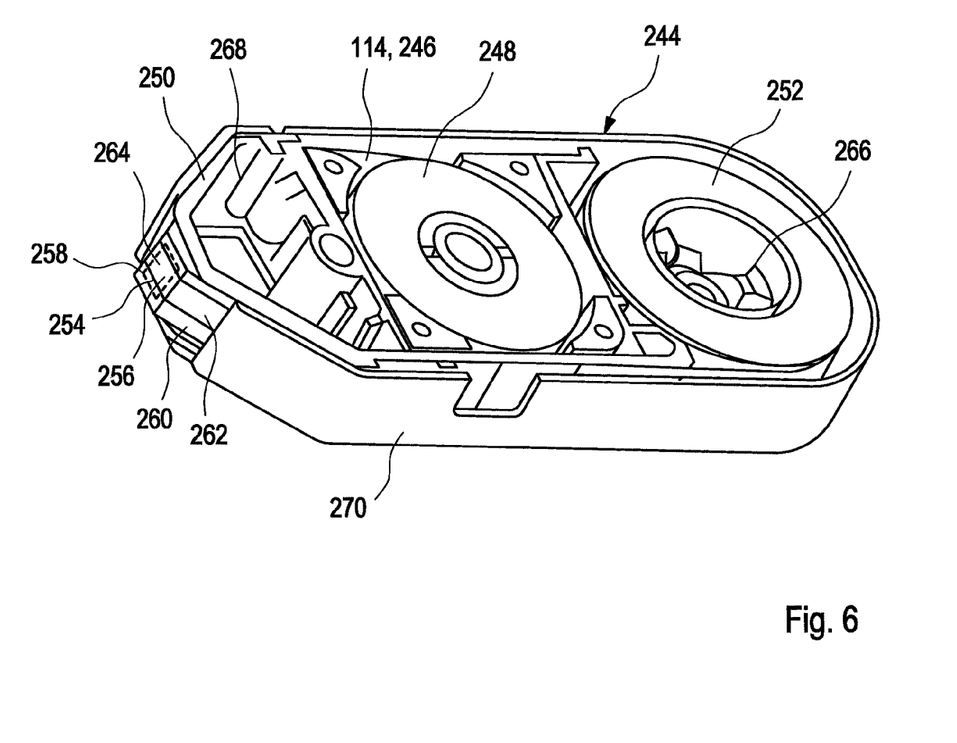
FIG. 6 shows an exemplary embodiment of a band cassette for use in the analytical test instrument according to FIG. 4.

FIG. 6 represents an exemplary embodiment of a possible band cassette 244, which may for example be used in the analytical test instrument 206 represented in FIG. 4 and which makes it possible for example to carry out a multiplicity of glucose analyses on liquid samples 220 (for example blood samples) obtained in situ by the patient himself. To this end, the band cassette 244 comprises a test element 114 in the form of an analytical test band 246. The analytical test band 246 can be drawn from a storage spool 248 and wound via a band guide 250 onto a winding spool 252. A test band section 254 of the analytical test band 246 is in this case stretched flat over a plane bearing frame 258 at a measurement site 256, in order to allow application of the liquid sample 220 on the front side, for example in the form of bodily fluid (for example blood or tissue fluid) and precise reflectometric measurement on the rear side.

The test band 246 has a transparent support band 260 which, for example, may correspond to the endless band 118 in FIG. 3 (in cut form). On the front side of this support band 260, for example similarly as at the top of FIG. 3, test fields are applied like labels, which may for example correspond to the test fields 196, 198 and 200 in FIG. 3. These test fields 262 may for example comprise dry chemicals, which respond to the analyte (for example glucose) in the applied liquid sample 220 (for example blood fluid) and lead to a measurable variation in the back-scattering of light when illuminated from the rear side. For example, the support band 260 may have a 5 mm wide and about 10 μm thick sheet, on the front side of which a detection film with a thickness of 50 μm is locally applied (for example labelled on).

For a measurement, measurement light is shone through a measurement opening 264 bordered by the bearing frame 258 and reflected, without optical elements such as lenses, filters or physically filled windows needing to be present inside the aperture region. The measurement opening 264 may however if necessary be surrounded by a shutter (not represented in FIG. 6). This allows defined rear-side focusing or alignment of an optical measurement unit (not contained in the band cassette 244) of the analytical test instrument 206 onto the test band section 254, which is exposed flatly through the measurement opening 264.

In order to transport the test fields 262 successively to the measurement site 256, a band drive of the analytical test instrument 206, engaging in a hub 266 of the winding spool 252, makes it possible to wind the test band 246 forward. Retaining forces of about 2 newtons are in this case generated by friction on the storage spool 248 and in the region of the band guide 250 (in particular on a push-through seal 268 there), so that the test band 246 is tensioned sufficiently to ensure that it bears flatly on the bearing frame 258.

The band guide 250 may for example be formed by an injection-moulded polypropylene part, which may likewise form a support body for the spools 248, 252. In order to cover the band guide 250 on the outside, a lid part 270 is provided which has a hole on a tapered narrow side wall for readily accessible of release of the bearing frame 258.

As explained above, either the test element 114, which is provided in cassetted form here, may be understood as the entire analytical test band 246 or individual test band sections 254 (for example test band sections respectively with one test field 262) may also be considered as such test elements 114. The test band 246 as a whole may respectively be marked or, as an alternative or in addition, marking of individual test band sections 254 may also be carried out by means of the method proposed above. If a separate device is used in order to read out defect markings, this may for example be integrated into the said optical measurement unit of the analytical test instrument 206. As an alternative, as described above, the excitation device 208 and the detection device 210 of the analytical test instrument 206 may also fulfill the function of reading out the defect markings in addition to the analysis function. Combinations of these two possibilities may also be envisaged, for example in the scope of a separate light source for reading out the defect markings, although with the detection device 210 simultaneously performing the defect readout task.

In this way, by using the band cassette 244 represented in FIG. 6, the analytical test instrument 206 may for example be adapted to interrogate whether the test band section 254 currently located in the measurement site 256 is defective, before carrying out the measurement. If it is, then for example the next test band section 254 is wound forward by corresponding actuation of the spools 248, 252, and the procedure is repeated for example by using the method described above with reference to FIG. 5.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary. Furthermore, all patents, patent applications, and publications cited herein are hereby incorporated by reference.

LIST OF REFERENCE NUMERALS 110 production device
112 test elements, divided up
114 test elements, cassetted
116 test elements, bandware
118 endless band
120 throughput direction
122 production device
123 bonding station for adhesive bonding of the test materials
124 central control unit
125 cutting device
126 processor
128 data memory
130 test device
132 camera
134 image recognition system
136 marking device
138 radiation source
140 light generator unit
142 circuitry compartment
144 individual light sources
146 fiber bundle
148 plastic fiber light guide
150 cross-section converter
152 application position
154 guide table
156 radiation
157 control device
158 dividing device
160 sorting device
162 packaging device
164 finished test element container
166 cassetting device
167 cutting and splicing device
168 electrical supply unit
176 UV light-emitting diodes
182 frame
184 openings
186 fiber ends
188 pattern
190 application module
195 positioning marks
196 test field
198 test field
200 test field
201 cutting lines
202 radiation-sensitive material
204 overall test field
206 analytical test instrument
208 excitation device
210 detection device
212 test field
214 test position
216 cover
218 housing
220 sample
222 drive and evaluation unit
224 control
226 display
228 user interface elements
230 interrogation device
232 provision of a new test field/test element
234 interrogate marking
236 test field/test element defective?
238 test field/test element defective
240 test field/test element defect-free
242 measurement
244 band cassette
246 analytical test band
248 storage spool
250 band guide
252 winding spool
254 test band section
256 measurement site
258 bearing frame
260 support band
262 test fields
264 measurement opening
266 hub
268 push-through seal
270 lid part

The invention claimed is:

1. A marking method for marking test elements, comprising: providing test elements adapted to detect at least one analyte in a sample; providing at least some of the test elements with a defect marking which contains digital information indicating the test elements are defective or non-defective, wherein the test elements include at least one radiation-sensitive material; exposing the test elements to at least one radiation, the radiation being adapted to induce said marking in the form of at least one optically detectable change in the at least one radiation-sensitive material; and wherein the at least one radiation-sensitive material is a test material of the test elements, wherein the test material defines the analytical functionality of a field of the test element and is adapted to change at least one of a measurable electrical property and a measurable optical property when the at least one analyte is present in the sample.

2. The marking method according to claim 1, wherein the defect marking provides only a binary or two-state status of the test elements indicating whether or not the test elements include one or more non-tolerable defects.

3. A marking system for marking defective test elements, comprising:
at least one test element adapted to detect at least one analyte in a sample, the at least one test element including a test field and at least one marking field formed separately from the test field, the at least one marking field comprising a radiation-sensitive material; a marking device adapted to provide the at least one test element with a defect marking which contains digital information indicating the at least one test element is defective or non-defective, wherein the marking device includes at least one radiation source for exposing the at least one test element to at least one radiation, the radiation being adapted to induce marking in the form of at least one optically detectable change in the radiation-sensitive material; and wherein the at least one radiation-sensitive material is a test material of the test elements, wherein the test material defines the analytical functionality of a field of the test element and is adapted to change at least one of a measurable electrical property and a measurable optical property when the at least one analyte is present in the sample.

4. The marking system according to claim 3, wherein the defect marking provides only a binary or two-state status of the at least one test element indicating whether or not the at least one test element includes one or more non-tolerable defects.

5. The marking system according to claim 3, further comprising at least one test device, the test device being adapted to subject the at least one test element to a defect check, the test device further being adapted to determine whether the test element includes one or more non-tolerable defects.

6. The marking system according to claim 3, wherein the radiation source comprises a plurality of modularly constructed individual light sources for generating ultraviolet light.

7. The marking system according to claim 3, wherein the marking device comprises at least one application position where the at least one test element is provided with the defect marking, the marking device further comprising at least one light waveguide for conducting the radiation from the radiation source to the application position.

8. The marking system according to claim 7, wherein the marking device includes a guide table in the application position, and at least two test elements being exposable simultaneously to the radiation in the guide table when in the application position.

9. The marking system according to claim 7, wherein the waveguide comprises at least one fiber light guide.

10. The marking system according to claim 9, wherein the at least one fiber light guide is a plastic fiber light guide.

11. The marking system according to claim 9, wherein a plurality of fiber light guides are combined to form a fiber bundle, the marking device further including at least one cross-section converter, the cross-section converter being adapted to hold the plurality of fiber light guides of at least one fiber bundle so that fiber ends of the fiber light guides are arranged in a predetermined pattern in the application position.

12. The marking system according to claim 11, wherein the pattern of the fiber ends includes at least one of the following patterns: a line pattern, a matrix pattern, and a rectangular matrix pattern.

13. A marking method for marking test elements, comprising: providing test elements adapted to detect at least one analyte in a sample; providing at least some of the test elements with a reject marking in response to determining the test elements are defective, wherein the test elements include a radiation-sensitive test material adapted to change at least one of a measurable electrical property and a measurable optical property when the at least one analyte is present in the sample; and exposing the test elements to at least one radiation, the radiation being adapted to induce said marking in the form of at least one optically detectable change in the radiation-sensitive test material.

14. The marking method according to claim 13, wherein the at least one radiation comprises electromagnetic radiation.

15. The marking method according to claim 14, wherein the electromagnetic radiation is ultraviolet radiation.

16. The marking method according to claim 15, wherein the ultraviolet radiation includes a wavelength range between 250 nm and 400 nm.

17. The marking method according to claim 15, wherein the ultraviolet radiation includes a wavelength range from 350 nm to 380 nm.

18. The marking method according to claim 13, wherein at least one of the following light sources is used to generate the at least one radiation: an incandescent lamp; a gas discharge lamp; a laser; a light-emitting diode; and a flash lamp.

19. The marking method according to claim 13, wherein the at least one optically detectable change comprises at least one of the following changes: a color change; a change of luminescence; a change of fluorescence; and a change of reflectivity.

20. The marking method according to claim 13, wherein the reject marking indicates the test elements include a non-tolerable defect due to deformation of the test elements.

21. The marking method according to claim 13, wherein the reject marking indicates the test elements include a non-tolerable defect due to incorrect application of a test material on the test elements.

22. The marking method according to claim 13, wherein the reject marking indicates the test elements include a non-tolerable defect due to an inhomogeneous test field on the test elements.

23. The marking method according to claim 13, wherein the reject marking indicates the test elements include a non-tolerable defect due to a non-constant layer thickness of a test field of the test elements.

24. The marking method according to claim 13, wherein the reject marking indicates the test elements include a non-tolerable defect due to an improper positioning of a test field on the test elements.

25. The marking method according to claim 13, wherein the reject marking indicates the test elements include a non-tolerable defect due to one or more of an electrical defect and an electrochemical defect of a test material of the test elements.

26. A marking system for marking defective test elements, comprising:

at least one test element adapted to detect at least one analyte in a sample, the at least one test element including a radiation-sensitive test material adapted to change at least one of a measurable electrical property and a measurable optical property when the at least one analyte is present in the sample; and a marking device adapted to provide the at least one test element with a reject marking in response to determining the at least one test element is defective, wherein the marking device includes at least one radiation source for exposing the at least one test element to at least one radiation, the radiation being adapted to induce marking in the form of at least one optically detectable change in the radiation-sensitive test material.

\* \* \* \* \*